(12) United States Patent
Shah et al.

(10) Patent No.: US 8,924,323 B2
(45) Date of Patent: Dec. 30, 2014

(54) SYSTEM AND METHOD FOR MANAGING INFORMATION OF BIOLOGICAL ENTITIES

(75) Inventors: Ajay Shah, Danville, CA (US); Srinivas Bolisetty, Frisco, TX (US); Xian-Wei Meng, Danville, CA (US); Ali G. Ozkabak, Pleasanton, CA (US); Anirban Ghosh, Fremont, CA (US); Kirti Jindal, Bangalore (IN); Krutin Boloor, Bangalore (IN); Ramesh Balakrishnan, Bangalore (IN); Manas Ajith Khare, Bangalore (IN); Parag Sangoi, Mumbai (IN)

(73) Assignee: Infosys Limited (IN)

( * ) Notice: Subject to any disclaimer, the term of this patent is extended or adjusted under 35 U.S.C. 154(b) by 176 days.

(21) Appl. No.: 13/366,810

(22) Filed: Feb. 6, 2012

(65) Prior Publication Data

US 2013/0013623 A1    Jan. 10, 2013

Related U.S. Application Data

(63) Continuation of application No. 13/165,038, filed on Jun. 21, 2011, now abandoned.

(51) Int. Cl.
*G06F 17/30* (2006.01)
*G06F 19/12* (2011.01)

(52) U.S. Cl.
CPC .......... *G06F 17/30595* (2013.01); *G06F 19/12* (2013.01)
USPC ............................................. 706/41; 706/45

(58) Field of Classification Search
CPC ................................ G06N 5/022; G06F 19/28
USPC ...................................................... 706/41, 45
See application file for complete search history.

(56) References Cited

PUBLICATIONS

Infosys, Developing a Cell Line Registration and Analysis System, Building Tomorrow's Enterprise, Case Study, Mar. 2009, pp. 1-4.*

* cited by examiner

*Primary Examiner* — Wilbert L Starks
(74) *Attorney, Agent, or Firm* — Lerner, David, Littenberg, Krumholz & Mentlik, LLP

(57) ABSTRACT

A system and method for managing, tracking and recording one or more biological process inputs, outputs and their derived forms is provided. The inputs pertaining to the biological process inputs, outputs and their derived forms are received and processed. The inputs include information related to the biological processes and the biological process inputs, outputs and their derived forms. The inputs further include information related to modifications in the biological process inputs, outputs and their derived forms. The inputs also include outputs of the biological processes. The inputs are processed by modifying the received inputs into a predefined format. Thereafter, the received inputs and processed inputs are stored. The stored inputs are accessed for managing, tracking and recording the biological processes, biological process inputs, outputs and their derived forms.

33 Claims, 12 Drawing Sheets

| Cell Line ▽ | Inventory ▽ | Reports ▽ | Help |

Register Original Eukaryotic Cell Line

Eukaryotic Cell Line Information

| Species | Human ▸ |
| Name Prefix(*) | HeLA-10 |
| Vendor Name (*) | ATCC ▸ | If Other Enter Name |
| Vendor Catalog # (*) | CRL-2572 ▸ |
| Description | |

Notebook Information | Growth Conditions | Tracking Information

| $CO_2$ Level | | % ▸ Units |
| Temperature | | °C ▸ Units |
| Media | |
| Antibiotic Resistances | |

[Save] [Clear]

SYSTEM AND METHOD FOR MANAGING INFORMATION OF BIOLOGICAL ENTITIES

CROSS-REFERENCE TO RELATED APPLICATIONS

The present application is a continuation of U.S. patent application Ser. No. 13/165,038, filed Jun. 21, 2011, the disclosure of which is incorporated herein by reference.

FIELD OF INVENTION

The present invention relates generally to biologics. More specifically, the present invention relates to managing, tracking and recording biological processes.

BACKGROUND OF THE INVENTION

Biological process outputs, also referred to as biological entities, such as cell lines, proteins, plasmids, antibodies, transgenics and so forth, are used for conducting scientific research. The research is conducted to identify the methods involved in biological processes such as transfection, transduction, cloning, hybridization, adaption, amplification, cloning, characterization, purification and so forth. The methods identified are used for further research and development activities such as purifying, characterizing, expressing, recombining, selecting, tailoring outputs for the development of drugs, therapies to combat disease manifestations and so forth.

The biological process outputs, more specifically the derived forms of biological process outputs, have diverse attributes. Further, the derived forms are typically developed via various multi-stage biological processes. Therefore, managing information associated with the biological process inputs, outputs and their derived forms is effort intensive.

The information related to biological processes is typically captured by researchers on index cards, hand note books, personal computers and so forth, which makes the information siloed and difficult to trace. Further there can be loss of valuable information when captured manually. Furthermore, the information related to the research work, associated biological processes, associated chemical processes and workflows etc. is not effectively captured. Also evidence of successful biological process inputs, outputs and their derived forms lying in freezers, are not easily traceable and hence lost. Therefore, the researchers confront information management issues, which in turn intensify tasks such as recording information, compiling information, associating information, filing an investigational New Drug or new biologic application and so forth.

Research starts by procuring bio-products and allied materials from outside vendors or partners. Owing to the scale, speed, and miniaturization of bio-systems and processes there is an enormous need to grow, spilt, derive the initial amounts and conduct individual processes in context to the hypothesis, so that the products brought from outside further expand into different varieties. Keeping track from the nascent product through the several generations of experiments is absolutely important for scientists. Additionally, these products are applied to a range of processes and often put to reuse and repurpose in context to the biological test performed on them. Hence, tracking of information related to the conducted research such as tracking information related to attributes of identified biological process inputs, outputs, properties of identified batches of biological outputs, lineage of biological process outputs and so forth is not efficiently performed when the information is captured manually. Deducing inferences based on the captured information therefore might lead to generation of erroneous information and loss of valuable information.

Biological process inputs, outputs can be procured, e.g. a cell line is procured to constitutively generate a protein, or a hybridoma is procured to develop an antibody. Biological processes involve physical transactions such as biological process output procurement, storage of one or more biological process outputs in freezers, depletion of biological process outputs, splits, merge, audit samples and so forth. Manually capturing information related to the inventory of biological process outputs and their derived forms used in the physical transactions is effort intensive and error prone.

Information captured for various biological processes is used for further research and development work. Collaboration of information captured in various biological processes which include trigger of events from one lab to another, notifying a specific group on sample availability, sharing performance of bio-process data with one or more groups, etc. These are not effectively performed and are typically absent when information is captured and shared manually.

Consequently, there is need for a system and a method for efficiently managing information related to biological processes. Also, the system should enable collaboration and cross referencing information of related biological process inputs, outputs and their derived forms. Further, the system should enable efficient searching, retrieving and tracking of biological process inputs, outputs and their derived forms. In addition, the system should enable efficient inventory management of biological process inputs, outputs and their derived forms. Further, the system should enable capturing of information from various information sources of molecular, cellular, structural, immunological, pharmacological and clinical information. Moreover, the system should enable generation of scanned reports of biological process output properties, location, quantity, and batch property description of biological property outputs.

SUMMARY OF THE INVENTION

A system and method for managing, tracking and recording one or more biological process inputs, outputs and their derived forms is provided. In various embodiments of the present invention, the system includes a user interface module to receive inputs pertaining to each of the one or more biological process inputs, outputs and their derived forms.

In various embodiments of the present invention, the information pertaining to the biological process inputs, outputs and their derived forms includes, but is not limited to, information related to the biological processes. The information related to the biological processes includes information that aids in executing the biological processes. Further, the information related to the biological processes also includes information that is used for executing the biological processes.

The information related to the biological process inputs, outputs and their derived forms further includes information related to the biological process inputs, outputs and their derived forms on which the biological process is performed. The information related to the biological process inputs, outputs and their derived forms further includes information related to modifications in the one or more biological process inputs, outputs and their derived forms in the biological process. The information related to the biological process inputs, outputs and their derived forms also includes information related to the outputs of the biological process.

In various embodiments of the present invention, the user interface module includes a biological process module to render information related to the biological process, biological process inputs, outputs and their derived forms.

The user interface module further includes a dashboard and reports module to render dashboards and reports generated for the one or more biological processes, biological process inputs, outputs and their derived forms.

The user interface module also includes a service module to render one or more services for managing, tracking and recording the biological process inputs, outputs and their derived forms.

In various embodiments of the present invention, the one or more services include a collaboration service for collaborating information related to the biological processes, biological process inputs, outputs and their derived forms. The one or more services further include a document management service for managing the documents created for the biological processes, biological process inputs, outputs and their derived forms.

In an embodiment of the present invention, the biological processes, biological process inputs, outputs and their derived forms are represented in at least one of a tabular form and a graphical form.

The one or more services further include a search service for searching at least one of the biological processes, biological process inputs, outputs and their derived forms. In an embodiment of the present invention, the search is performed based on inputs for one or more graphics stored in a data repository.

In various embodiments of the present invention, the system includes a processing module to process the received inputs. The inputs are processed into a predefined format.

In various embodiments of the present invention, the processing module includes a workflow module to generate one or more workflows for each biological process based on the inputs received for the biological process. The system further includes an infrastructure module to validate the generated workflows based on one or more validation protocols. The infrastructure module also adds a predefined level of security to the generated workflows based on predefined conditions. Further, the information module creates metadata for the generated workflows.

In various embodiments of the present invention, the processing module includes a registration module to register each of the one or more biological processes, biological process inputs, outputs and their derived forms. The registration is performed by assigning a unique identifier to each of the one or more biological processes, biological process inputs, outputs and their derived forms. The system further includes a validation module to validate the registered business processes, business process inputs, outputs and their derived forms.

In various embodiments of the present invention, the system includes an inventory module to manage inventory of the biological process inputs, outputs and their derived forms. The managing of inventory includes registering the inventory of the biological process inputs, outputs and their derived forms. Further, the inventory details of the biological process inputs, outputs and their derived forms are updated based on modifications in the biological process inputs, outputs and their derived forms. The inventory details are also updated based on outputs of the biological processes. The inventory module further audits the inventory details.

In an embodiment of the present invention, the inventory module generates one or more container maps for the biological process inputs, outputs and their derived forms. Each container map represents storage information of the corresponding biological process inputs, outputs and their derived forms. The inventory module also manages the inventory details of one or more biological process inputs, outputs and their derived forms stored in one or more freezers.

In another embodiment of the present invention, the inventory module also updates the inventory details based on procurement of one or more biological process inputs, outputs and their derived forms. The procurement is performed based on procurement inputs received through the user interface module. Further, the inventory details are updated based on depletion, thawing and discarding of the biological process inputs, outputs and their derived forms.

In various embodiments of the present invention, the system includes a data repository to store the received inputs and the processed inputs. The stored inputs can be accessed by the user interface module.

In various embodiments of the present invention, the data repository interacts with a data service module to provide one or more data services for processing the received inputs. The data repository further interacts with a mapping module to generate one or more genealogy maps for each of the one or more business process inputs, outputs and their derived forms. Each genealogy map represents the association between the corresponding biological process inputs, outputs and their derived forms and the outputs of the biological process. The data repository further interacts with a framework component to enable access of the stored inputs and the one or more data services.

In various embodiments of the present invention, the data repository the data repository includes an Entity-Attribute-Value model to store information related to the biological processes, biological process inputs, outputs and their derived forms. The data repository also includes a relational data model to store inventory details of the biological process inputs, outputs and their derived forms. The data repository further includes a semantic model configured to store relationships between the biological processes, biological process inputs, outputs and their derived forms.

In an embodiment of the present invention, the system includes a web service module to facilitate interaction between one or more users and the system through the user interface module over a network.

In another embodiment of the present invention, the system includes a knowledge base of biological process inputs, outputs and derived forms to collaborate information related to the biological processes, biological process inputs, outputs and their derived forms.

In various embodiments of the present invention, the system includes a server infrastructure to facilitate communication between one or more users and the system through the user interface module.

In various embodiments of the present invention, the method for managing, tracking and recording the biological process inputs, outputs and their derived forms includes gathering inputs pertaining to the biological process inputs, outputs and their derived forms.

In various embodiments of the present invention, the method includes processing the gathered inputs by modifying the gathered inputs into a predefined format. In an embodiment of the present invention, processing the gathered inputs includes updating the information related to the one or more biological process inputs, outputs and their derived forms based on inputs related to one or more modifications in the biological processes, biological process inputs, outputs and their derived forms. In an embodiment of the present invention, the method includes tracking the one or more biological process inputs, outputs and their derived forms. Tracking is performed by viewing the information related to the biological process, biological process inputs, outputs and their derived forms.

In an embodiment of the present invention, the method includes managing inventory of the one or more biological process inputs, outputs and their derived forms.

In an embodiment of the present invention, the method includes searching for at least one of the one or more biological processes, biological process inputs, outputs and their derived forms. In another embodiment of the present invention, the search is performed based on user-defined queries.

In various embodiments of the present invention, the method includes storing the gathered inputs and the processed inputs. In various embodiments of the present invention, the method includes viewing the stored inputs.

In an embodiment of the present invention, the method includes registering each of the one or more biological processes, biological process inputs, outputs and their derived forms. The registration is performed by assigning a unique identifier to each biological process, biological process inputs, outputs and their derived forms.

In an embodiment of the present invention, the processing of the gathered inputs includes developing one or more genealogy maps for each biological process input, output and their derived forms.

BRIEF DESCRIPTION OF THE DRAWINGS

The present invention is described by way of embodiments illustrated in the accompanying drawings wherein:

FIG. 3C illustrates an exemplary screenshot for recording and registering one or more biological processes, biological process inputs, outputs and their derived forms;

FIGS. 3D, 3E, 3F and 3G illustrate exemplary screenshots for managing inventory of the one or more biological process inputs, outputs and their derived forms;

DETAILED DESCRIPTION

Figure 1:
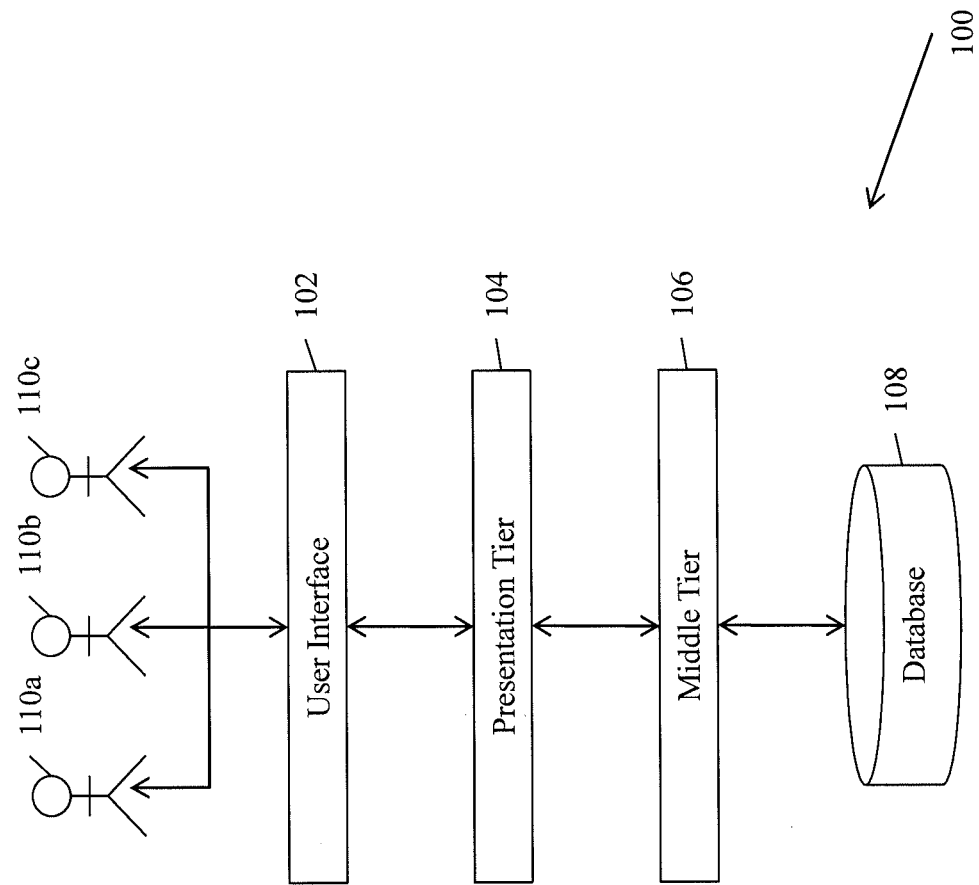
FIG. 1 illustrates a block diagram of a system for managing, tracking and recording of one or more biological process inputs, outputs and their derived forms, in accordance with an embodiment of the present invention.

A system and method for managing, tracking and recording information of scientific research is provided. The present invention more specifically provides a system and method for managing, tracking and recording one or more biological process inputs, outputs and their derived forms. Exemplary scenarios in which the present invention may be implemented include, but are not limited to, scientific research and development, biological laboratories and chemistry laboratories.

The present invention may also be implemented for biotechnology applications, applied life sciences, healthcare companies that conduct molecular diagnostics. The present invention may also be applicable for agriculture-based industries, specialty biologics and consumer product and goods industries producing cereals, beverages, snacks etc., wherein there is a need for isolating active ingredients from plant and other species sources through active molecular research. Further, the active molecular research includes analysis of proteins, plasmids, cell systems, antibodies, and model organisms to test and generate markers as active ingredients for their products.

Efficient managing, tracking and recording of information of biological process inputs, outputs and their derived forms is performed via various automated steps.

In an embodiment of the present invention, the system and method disclosed provides recording and registering of one or more biological process inputs, outputs and their derived forms.

In another embodiment of the present invention, the system and method disclosed provides one or more genealogy maps for each biological process.

In yet another embodiment of the present invention, the system and method disclosed provides capability to modify information of the biological process inputs, outputs and their derived forms.

In yet another embodiment of the present invention, the system and method disclosed provides viewing information of one or more biological processes, one or more biological process inputs, outputs and their derived forms.

In yet another embodiment of the present invention, the system and method disclosed provides tracking of the one or more biological processes, the one or more biological process inputs, outputs and their derived forms.

In yet another embodiment of the present invention, the system and method disclosed provides managing inventory of the one or more biological process inputs, outputs and their derived forms.

In yet another embodiment of the present invention, the system and method disclosed provides managing workflows of the one or more biological processes.

In yet another embodiment of the present invention, the system and method disclosed provides searching of one or more biological processes and one or more biological process inputs, outputs and their derived forms.

In yet another embodiment of the present invention, the system and method disclosed provides collaborating information of the one or more biological processes and the one or more biological process inputs, outputs and their derived forms.

Hence, the present invention enables efficient management, tracking and recording of biological process inputs, outputs and their derived forms. Further, the present invention enables efficient management of inventory of the biological process inputs, outputs and their derived forms. In addition, the present invention enables efficient collaboration of information captured for the biological processes and the biological process inputs, outputs and their derived forms.

The disclosure is provided in order to enable a person having ordinary skill in the art to practice the invention. Exemplary embodiments herein are provided only for illustrative purposes and various modifications will be readily apparent to persons ordinarily skilled in the art. The general principles defined herein may be applied to other embodiments and applications without departing from the spirit and scope of the invention. The terminology and phraseology used herein is for the purpose of describing exemplary embodiments and should not be considered limiting. Thus, the present disclosure is to be accorded the widest scope encompassing numerous alternatives, modifications and equivalents consistent with the principles and features disclosed herein. For purpose of clarity, details relating to technical material that is known in the technical fields related to the invention have been briefly described or omitted so as not to unnecessarily obscure the present invention.

The present invention would now be discussed in context of embodiments as illustrated in the accompanying drawings.

FIG. 1 illustrates a block diagram of a system for managing, tracking and recording of one or more biological process inputs, outputs and their derived forms, in accordance with an embodiment of the present invention.

System 100 is configured to manage, track and record information of the biological processes inputs, outputs and their derived forms. Hereinafter, managing encompasses the meaning of the terms managing and tracking. Biological process inputs, outputs such as, but not limited to, cell lines, plasmids, antibodies, proteins and transgenics are used for conducting scientific research and development. In an embodiment of the present invention, biological process inputs, outputs and their derived forms are also referred to as biological entities. The biological process inputs and outputs are modified via one or more biological processes for creating one or more derived forms of biological process outputs. For example, a transfection process is performed for deriving a new cell line from a parent cell line. This new derived cell line expresses a new or altered protein. Examples of biological processes include transfection, transduction, amplification, cloning, hybridoma development, adaptation, purification and so forth. Further, each biological process may include one or more stages. For example, a protein obtained may be further processed via a protein purification process, wherein the protein purification process includes recording and registering of a conceptual protein by tagging the protein with a unique identifier, characterization of the protein, purification of protein, recoding and registering inventory information of the purified protein and so forth.

The managing, tracking and recording of the biological process inputs, outputs and their derived forms is enabled through a user interface 102 via one or more architecture tiers, wherein the one or more architecture tiers include a presentation tier 104, a middle tier 106 and a database 108.

Users such as, but not limited to, user 110*a*, user 110*b* and user 110*c*, access system 100 via user interface 102. In various embodiments of the present invention, the users are one of, but not limited to, scientific researchers, scientific research administrators and system administrators, wherein scientific researchers include biologists and chemists.

User interface 102 is configured to provide an interactive interface for accessing system 100. In an embodiment of the present invention, user interface 102 is one of, but not limited to, a Graphical User Interface (GUI) and a Web-based User Interface (WUI).

Presentation tier 104 is configured to render information via user interface 102. In an embodiment of the present invention, the information rendered includes, but is not limited to, information related to biological processes, biological process inputs, outputs and their derivative forms, collaboration service information, document management service information and so forth. In various embodiments of the present invention, the presentation tier is a user interface module configured to receive inputs pertaining to each of the one or more biological process inputs, outputs and their derived forms. The user interface module is further configured to access the inputs stored in a data repository.

Presentation tier 104 is further configured to capture information related to biological processes, the biological process inputs, outputs and their derived forms. In various embodiments of the present invention, information is captured for one or more of—recording and registering of biological processes, biological process inputs, outputs and their derived forms, genealogy of biological processes, biological process inputs, outputs and their derived forms, modifications of biological processes, biological process inputs, outputs and their derived forms, tracking of biological processes, biological process inputs, outputs and their derived forms, inventory levels of biological process inputs, outputs and their derived forms, procurement requests for biological process inputs, outputs and their derived forms, depletion of biological process inputs, outputs and their derived forms, workflows of biological processes and search requests for biological processes, biological process inputs, outputs and their derived forms. The captured information is stored in database 108.

Presentation tier 104 is further configured to interact with middle tier 106 and database 108 and render the information obtained from the interaction via user interface 102.

Middle tier 106 is configured to process information related to the biological processes, biological process inputs, outputs and their derived forms. In various embodiments of the present invention, the middle tier is a processing module configured to process the received inputs into a predefined format. The processing of information includes modifying the information captured via presentation tier 104 into predefined formats. For example, the registration information captured via presentation tier 104 through user interface 102 is used for registering the biological processes, biological process inputs, outputs and their derived forms. The processed information is stored in database 108.

Database 108 is configured to store information associated with the business processes, biological process inputs, outputs and their derived forms. In various embodiments of the present invention, the database is a data repository configured to store the received inputs and the processed inputs. In an embodiment of the present invention, an electronic record of biological process inputs, outputs and their derived forms generated at the end of the biological processes or used in the biological processes. The associated properties and notebook information for these biological process inputs, outputs and their derived forms are also captured as electronic record.

In various exemplary embodiments of the present invention, the biological processes inputs, outputs are captured in line with the business process. For example, an original cell line is captured as one procured from a vendor; a derived cell line is captured as one derived by one or more biological processes such as transfection, transduction, amplification, adaptation, cloning, hybridoma development and so forth; a protein is identified with its sequence information, structure and biochemical/biophysical characteristics and so forth; a tissue is associated by the functionality it carries. All the steps in the business process from a cell line to its derived outputs to the proteins it expressions, either singularly or as a tissue are associated by using a semantic technology. Further, the captured information is stored in database 108. Also, the semantic technology is used for managing, tracking and recording inventory of biological process inputs, outputs and their derived forms.

In an embodiment of the present invention, database 108 is based on an Entity-Attribute-Value (EAV) model. Further, database 108 is one of, but not limited to, a relational database, operational database, analytical database, external database, navigational database and document oriented database. In an exemplary embodiment of the present invention, database 108 is an Oracle® database. Dynamic form builder functionality is used for rendering information stored in database 108 via presentation tier 104. The dynamic form builder functionality enables addition, deletion or modification in biological processes, biological process inputs, outputs and derived forms of biological process outputs to be reflected automatically on presentation tier 104. The information captured via presentation tier 104 and processed via middle tier 106 is stored in database 108. In an embodiment of the present invention, database 108 includes a set of tables for storing information. For example, database 108 includes tables for storing information along with the metadata associated with the biological processes, the biological process inputs, outputs and their derived forms. The information is stored in different value tables for each property in a row. Database 108 is further configured to enable retrieval of the stored information, wherein the information retrieved is rendered via user interface 102 through presentation tier 104. For example, the information related to a cell line stored in database 108 is rendered to a user via user interface 102.

Figure 2:
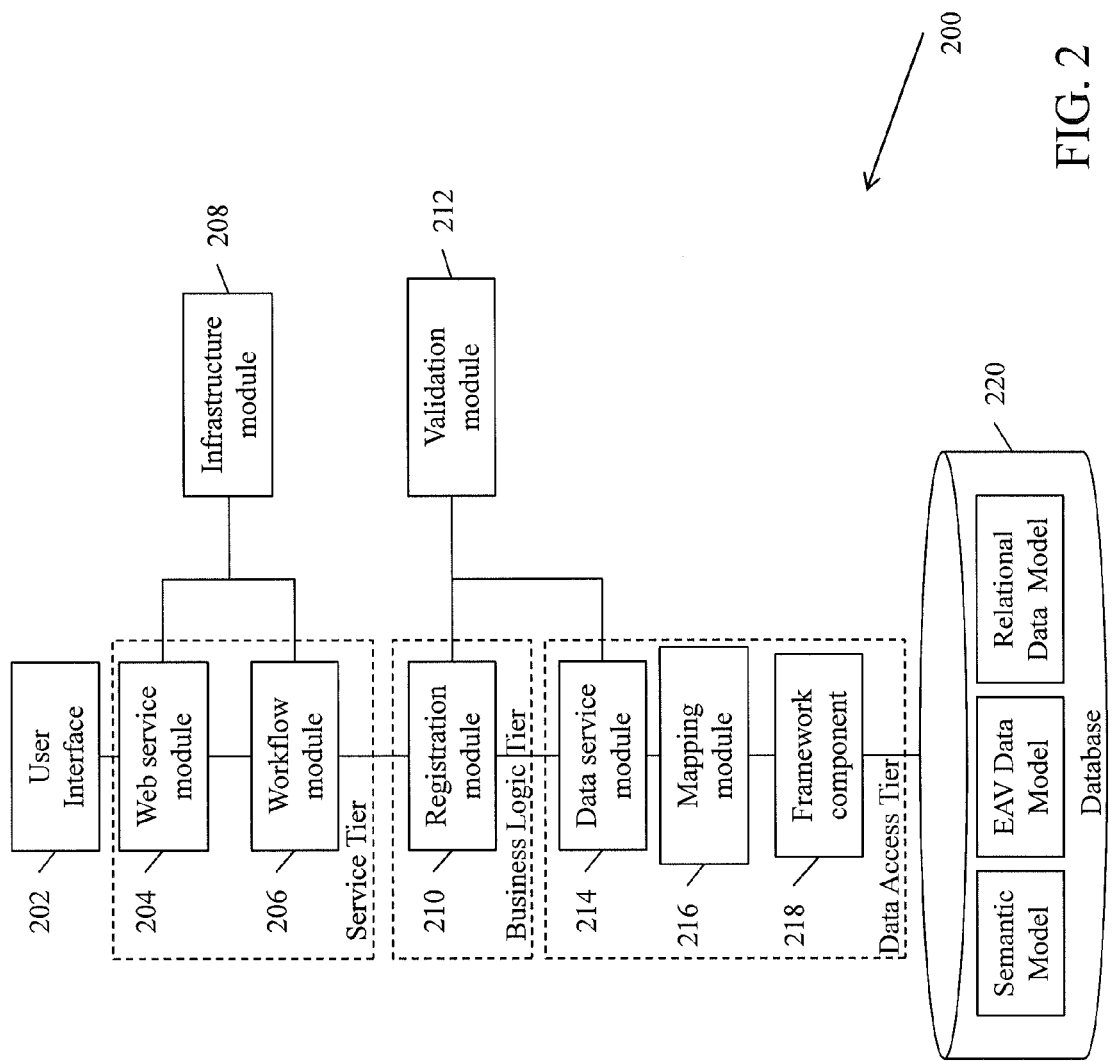
FIG. 2 illustrates a block diagram of the system for managing, tracking and recording of one or more biological process inputs, outputs and their derived forms, in accordance with another embodiment of the present invention.

FIG. 2 illustrates a block diagram of the system for managing, tracking and recording of one or more biological process inputs, outputs and their derived forms, in accordance with another embodiment of the present invention.

System 200 includes a user interface 202, a web service module 204, a workflow module 206, an infrastructure module 208, a registration module 210, a validation module 212, a data service module 214, a mapping module 216, a framework component 218 and a database 220.

System 200 is accessed via user interface 202. User interface 202 enables interaction with one or more architecture tiers, wherein the one or more architecture tiers include service tier, business logic tier and data access tier.

The service tier includes web service module 204 and workflow module 206. Web service module 204 is configured to enable managing information of one or more biological processes via user interface 202 over a network, wherein the network can be one of, but not limited to, a local area network, an office area network, a wide area network, intranet and internet. For example, web service module 204 enables registration of biological processes, the biological process inputs, outputs and their derived forms via user interface 202. Workflow module 206 is configured to enable creation of workflows for one or more biological processes via user interface 202. In various embodiments of the present invention, the workflow module is configured to generate one or more workflows for the biological processes. For example, workflow module 206 enables creation of a workflow for a protein purification process via user interface 202. The created workflows are stored in database 220 and can be accessed via user interface 202. The users can modify the existing workflows by using workflow module 206 via user interface 202.

Infrastructure module 208 is configured to process the workflows created using workflow module 206. The processing of workflows includes validating the created workflows, providing a predefined level of security to the created workflows based on predefined conditions and creating metadata for the workflows. The validation is performed based on validation protocols. The predefined level of security enables user based access of the system. For example, the system administrator can perform administrative changes.

The business logic tier includes registration module 210, which is configured to register biological processes, the biological process inputs, outputs and their derived forms. Validation module 212 is configured to validate the registration of the biological processes, the biological process inputs, outputs and their derived forms.

The data access tier includes data service module 214, mapping module 216 and framework component 218.

Data service module 214 is configured to provide data services which enable storage of information of biological processes, biological process inputs, outputs and their derived forms. The information stored includes information related to attributes and properties of biological processes, biological process inputs, outputs and their derived forms. The information stored further includes instance values of biological processes, biological process inputs, outputs and their derived forms. For example, data service module 214 enables storage of information of a protein, wherein the information includes details related to the protein such as name, identification number and so forth, properties of the protein such as melting point, freezing point, family, structure and so forth and instance value of protein such as storage details including container information, quantity and so forth. In an exemplary embodiment of the present invention, data service module 214 provides a biological EAV model based data service.

Mapping module 216 is configured to develop genealogy maps for the biological processes, the biological process inputs, outputs and their derived forms. The genealogy maps are developed based on the information captured for biological processes, biological process inputs, outputs and their derived forms and the modifications in biological processes, biological process inputs, outputs and their derived forms. The genealogy maps represent the association between related biological processes, the biological process inputs, outputs and their derived forms. In other words, genealogy maps represent the association of biological processes, the biological process inputs, outputs and their derived forms Framework component 218 is configured to enable access to the information related to the biological processes, the biological process inputs, outputs and their derived forms and data services provided via data service module 214. In an exemplary embodiment of the present invention, framework component 218 is an ADO.net® component.

Database 220 is configured to store the information related to the biological process. The information stored in database 220 is rendered to user interface 202 through the web services module 204 through the one or more architecture tiers.

In various embodiments of the present invention, database 220 includes, but not limited to, an EAV data model, a relational data model and a semantic model. The EAV data model is configured to store the information related to the biological processes, the biological process inputs, outputs and their derived forms. The relational data model is configured to store the inventory details of the biological process inputs, outputs and their derived forms. The semantic model is configured to store the relationships between the biological processes, the biological process inputs, outputs and their derived forms.

Figure 3A:
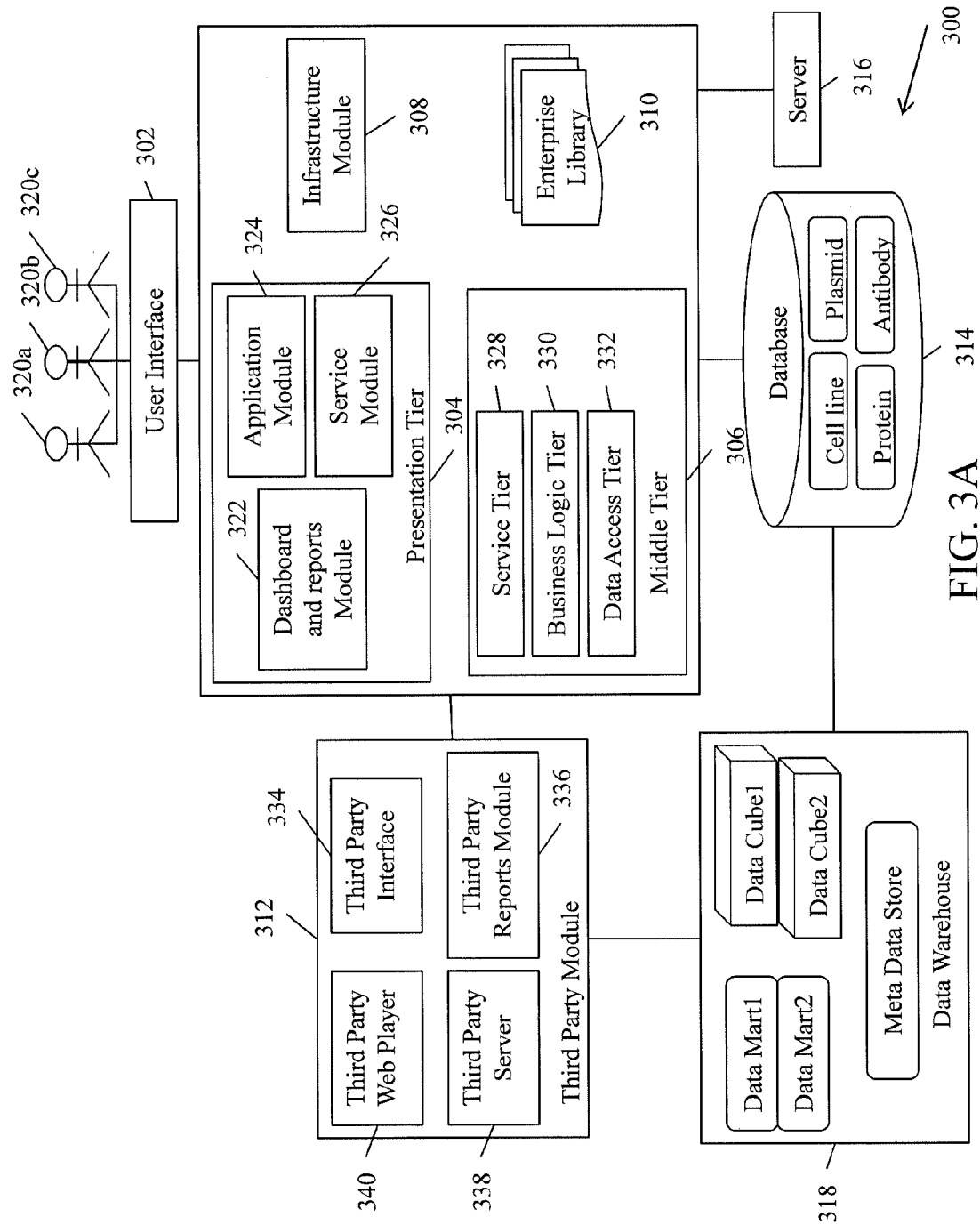
FIG. 3A illustrates a block diagram of the system for managing, tracking and recording of one or more biological process inputs, outputs and their derived forms, in accordance with yet another embodiment of the present invention.

FIG. 3A illustrates a block diagram of the system for managing, tracking and recording of one or more biological process inputs, outputs and their derived forms, in accordance with yet another embodiment of the present invention.

System 300 includes a user interface 302, a presentation tier 304, a middle tier 306, a third party module 308, an infrastructure module 310, an enterprise library 312, a database 314, a server 316 and a data warehouse 318.

User interface 302 is configured to provide an interactive interface for accessing system 300. Users such as user 320*a*, user 320*b* and user 320*c* access system 300 for managing information of biological processes, biological process inputs, outputs and their derived forms. For accessing system 300 users need to login by providing login and password details. User interface 302 provides a login interface for entering login and password details. In an embodiment of the present invention, system 300 enables a single sign-on via user interface 302, wherein users can access various features of system 300 based on a single login. Post validation of the login and password details user interface 302 renders a customized user interface based on the provided login and password details. The customized user interface includes a predefined set of system components defined based on the access history of the user. For example, the customized user interface provides a workflow based system through which a user can work on various biological processes such as derivation, purification, characterization, inventory, etc. In an embodiment of the present invention, user interface 302 renders a customized user interface for a biological entity component, various process components such as derivation, purification, characterization, inventory and so forth, a reports component, a search component and genealogy map component.

Presentation tier 304 is configured to render information via user interface 302. Presentation tier 304 includes a dashboard and reports module 322, an application module 324 and a service module 326.

Dashboard and reports module 322 is configured to render information related to dashboards and reports of biological processes, biological process inputs, outputs and their derived forms. In an embodiment of the present invention, dashboard and reports module 322 renders information related to dashboards created for biological process inputs, outputs and their derived forms and associated biological processes, research conducted on biological process inputs, outputs and their derived forms and information collaborated for biological processes and biological process inputs, outputs and their derived forms. Further, dashboard and reports module 322 renders reports created for biological process inputs, outputs and their derived forms and associated biological processes. For example, dashboard and reports module 322 renders genealogy maps created for biological process inputs, outputs and their derived forms, experimental analysis details of biological processes and so forth. In an embodiment of the present invention, the reports are presented in a tabular form. In another embodiment of the present invention, the information in the reports is presented in a graphical form. Further, scanned reports are generated on specific process output properties, or about the location, quantity, and batch property description of outputs Application module 324 is configured to render information related to biological processes and biological process inputs, outputs and their derived forms. In various embodiments of the present invention, the application module is a biological process module configured to render information related to the biological process, biological process inputs, outputs and their derived forms. For example, application module 324 renders biological process inputs, outputs and their derived forms details including, but not limited to, name, type, species, source, tissue type, passage number, description, process details and so forth. In an exemplary embodiment of the present invention, application module 324 is configured to render information related to one or more biological process inputs, outputs and their derived forms and the one or more biological processes including cell lines, plasmids, antibodies, proteins, derivation, purification, characterization and so forth.

Service module 326 is configured to provide services via user interface 302. In an embodiment of the present invention, service module 326 provides a collaboration service, a web service, a document management service and a search service.

The collaboration service enables knowledge management, wherein information related to biological processes, biological process inputs, outputs and their derived forms is collaborated and rendered to users via user interface 302. The collaboration service enables selection of biological processes and biological process inputs, outputs and their derived forms for which information needs to be retrieved. Upon selection of the biological processes or biological process inputs, outputs and their derived forms a corresponding interface is rendered, wherein the interface renders the information gathered for the corresponding biological process inputs, outputs and their derived forms and the associated biological processes. Further, information can be collaborated for batches of biological process inputs, outputs and their derived forms. For example, the research information related to a batch of cell lines is gathered using the collaboration service and thereafter presented via user interface 302. In an embodiment of the present invention, cross referencing information on another related biological process output by fetching data from another similar system, capturing external curate information for industry validated data is performed. In another embodiment of the present invention, collaboration of information is performed through a knowledge base of biological process outputs. For example, each protein has molecular, cellular, structural, immunological, pharmacological, clinical information captured and updated from various sources like Wikipedia®, external sites, internal knowledge systems or digital libraries. This knowledge is further annotated by scientific researchers. In an exemplary embodiment of the present invention, the collaboration is performed through Kinase Wiki®, which includes information for each member of protein in the Kinase family. In another exemplary embodiment of the present invention, the collaboration is performed through Uniprot®.

In an exemplary embodiment of the present invention, collaboration of information captured in various biological processes which include trigger of events from one lab to another, notifying a specific group on sample availability, sharing performance of bio-process data with one or more groups, etc are specific elements of collaboration that can enabled by system 300. Exemplary collaboration scenarios include, but are not limited to, handing samples from cell biology lab to biochemistry lab for purification; receiving alerts on non availability of specific plasmid construct; expressing large amount of starting materials; measuring target discovery group members properties and alerting crystallography group based on the measurement, etc.

The web service enables managing information of biological process inputs, outputs and their derived forms over a network such as intranet, local area network, office area network, wide area network, internet and so forth.

The document management service enables management of documents related to the biological processes and biological process inputs, outputs and their derived forms. In various biological processes, documents such as workflow documents, process detail documents, mapping images and so forth are created. The document management service enables management of the created documents.

The search service enables searching of biological processes and biological process inputs, outputs and their derived forms. In an embodiment of the present invention, the search service enables searching of biological processes, biological process inputs, outputs and their derived forms in one or more predefined locations. Examples of predefined locations include, but are not limited to, local database, global database which stores information related to various local databases and so forth for biological processes and biological process inputs, outputs and their derived forms. In an embodiment of the present invention, search is performed based on inputs for searching graphics such as spectrograph images, blot scans etc. stored in the database. In another embodiment of the present invention, search is performed based on user-defined queries. The users can define their own query and query results. Dynamic form builder functionality is leveraged to implement user-defined query. The users can save these queries which can be referenced at a later date. In an embodiment of the present invention, semantic technology is used for generating the genealogy maps.

Figure 3B:
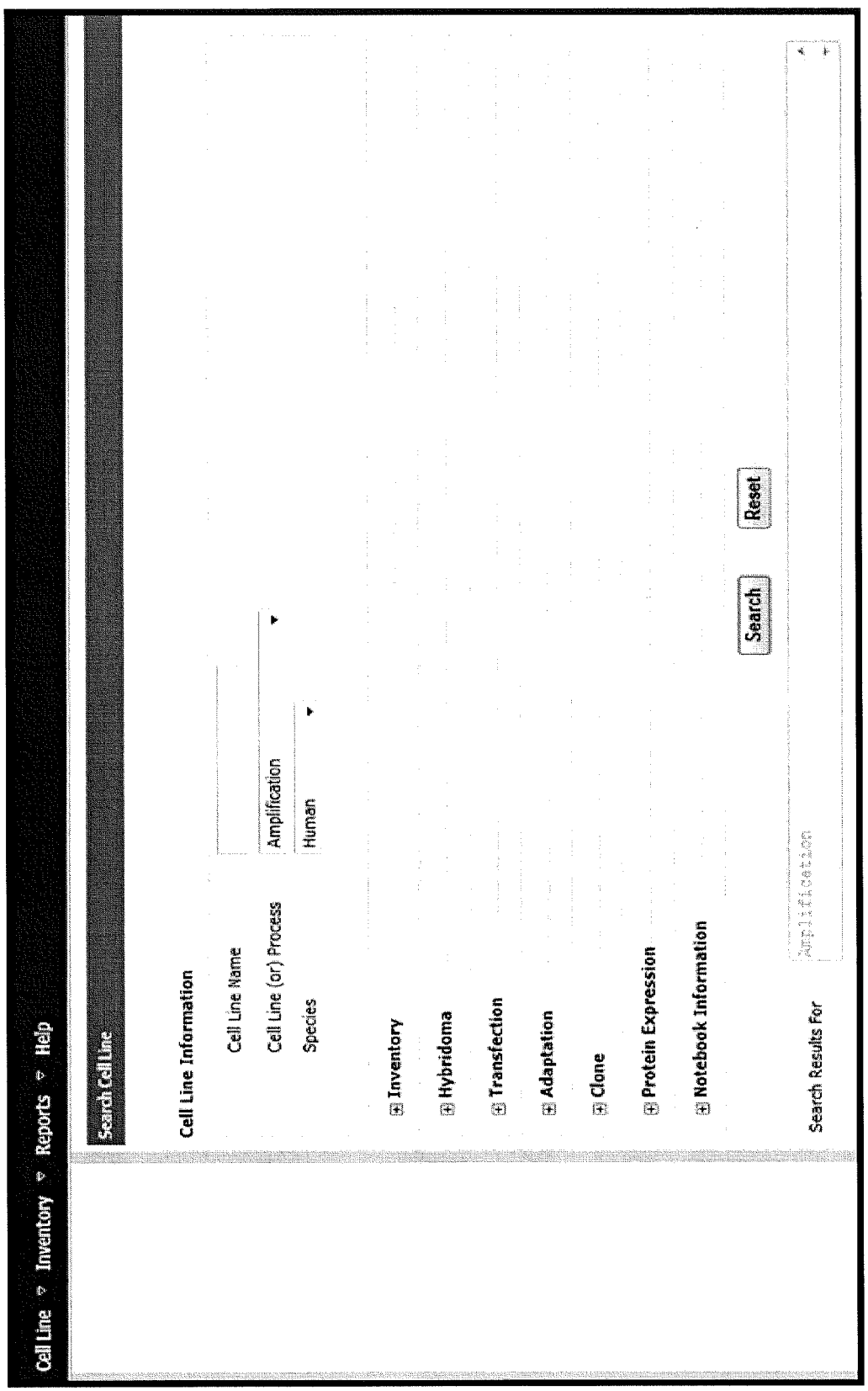
FIG. 3B illustrates an exemplary screenshot of a search service.
Figure 3D:
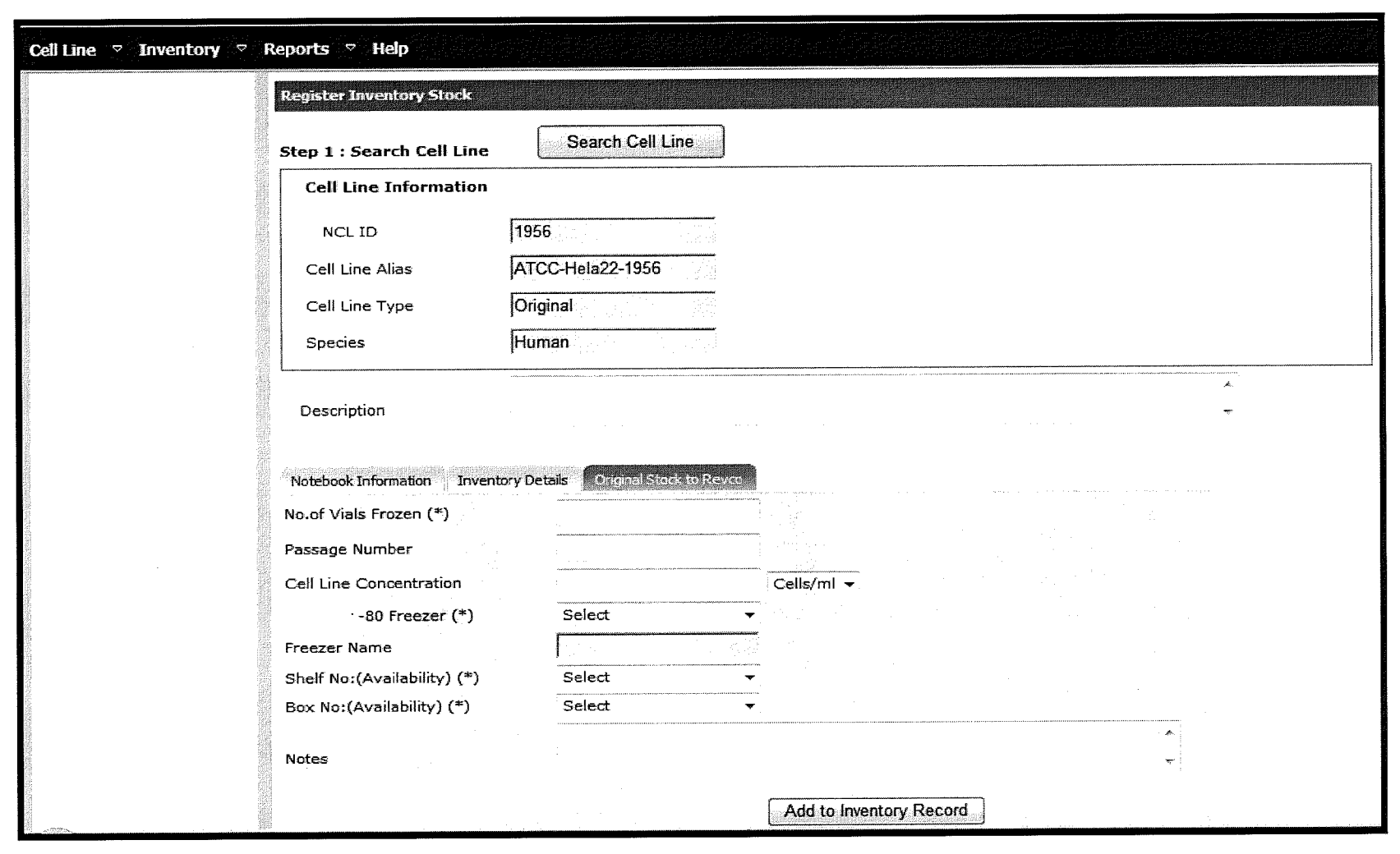
Figure 3E:
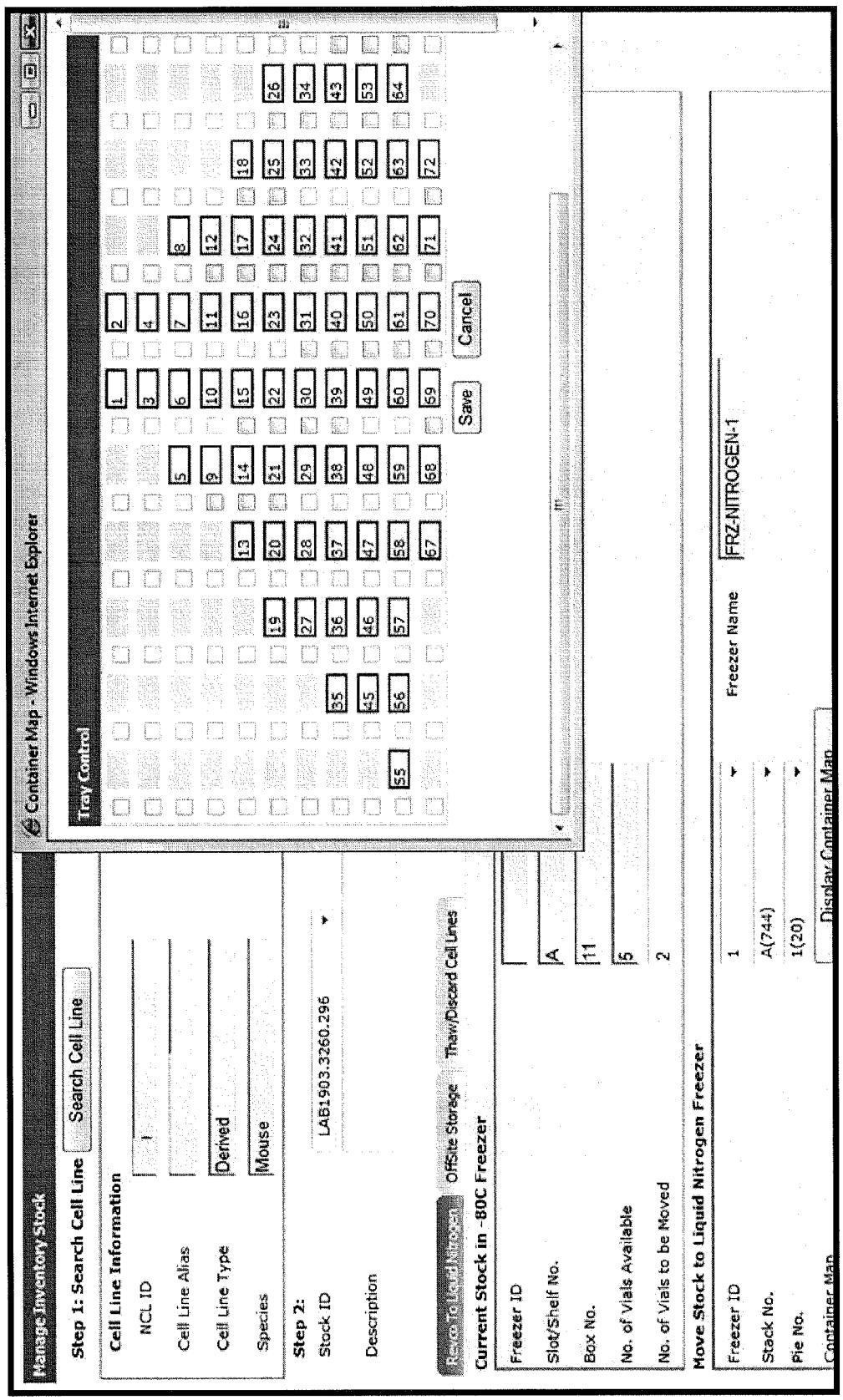
Figure 3F:
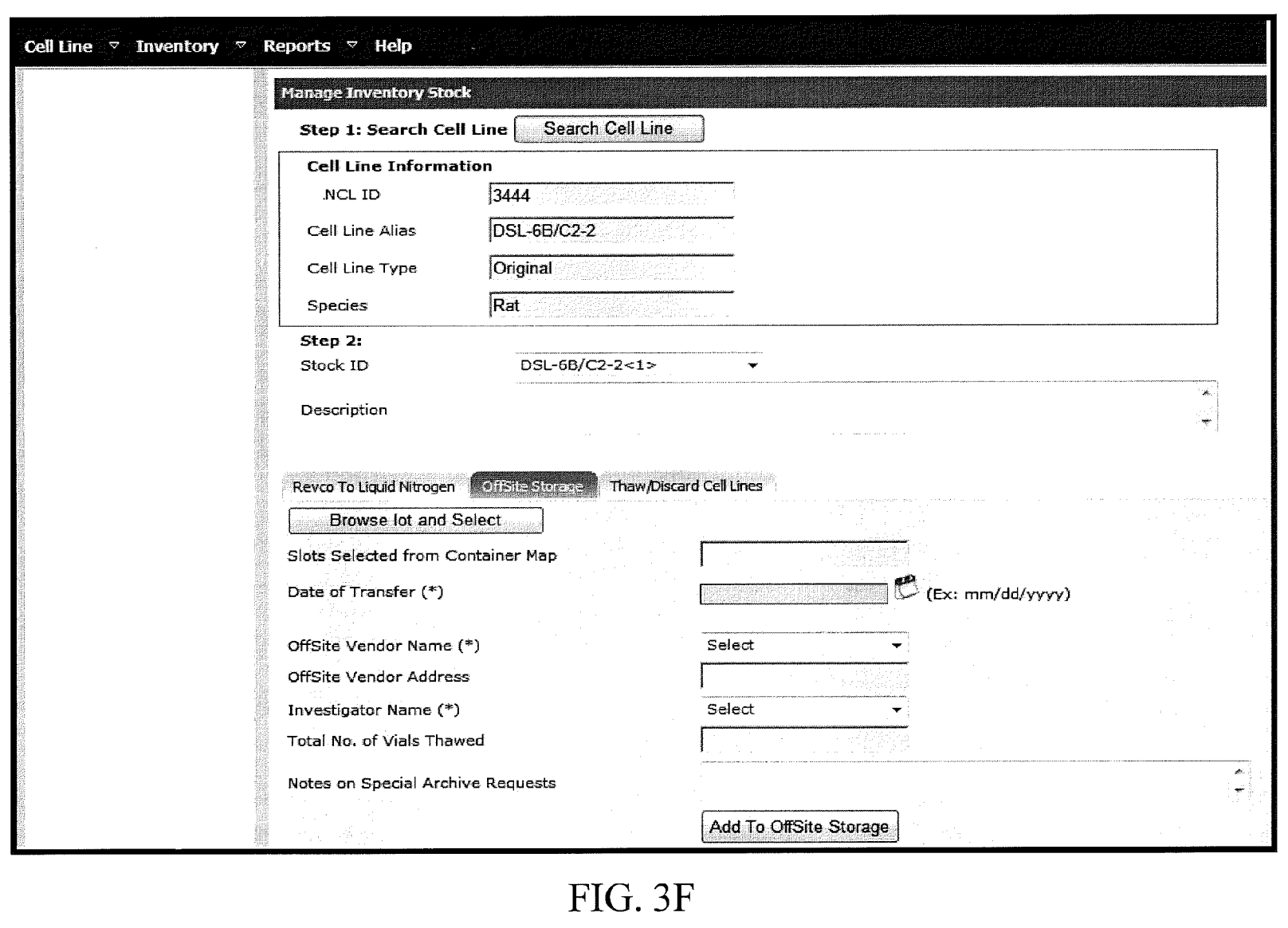
Figure 3G:
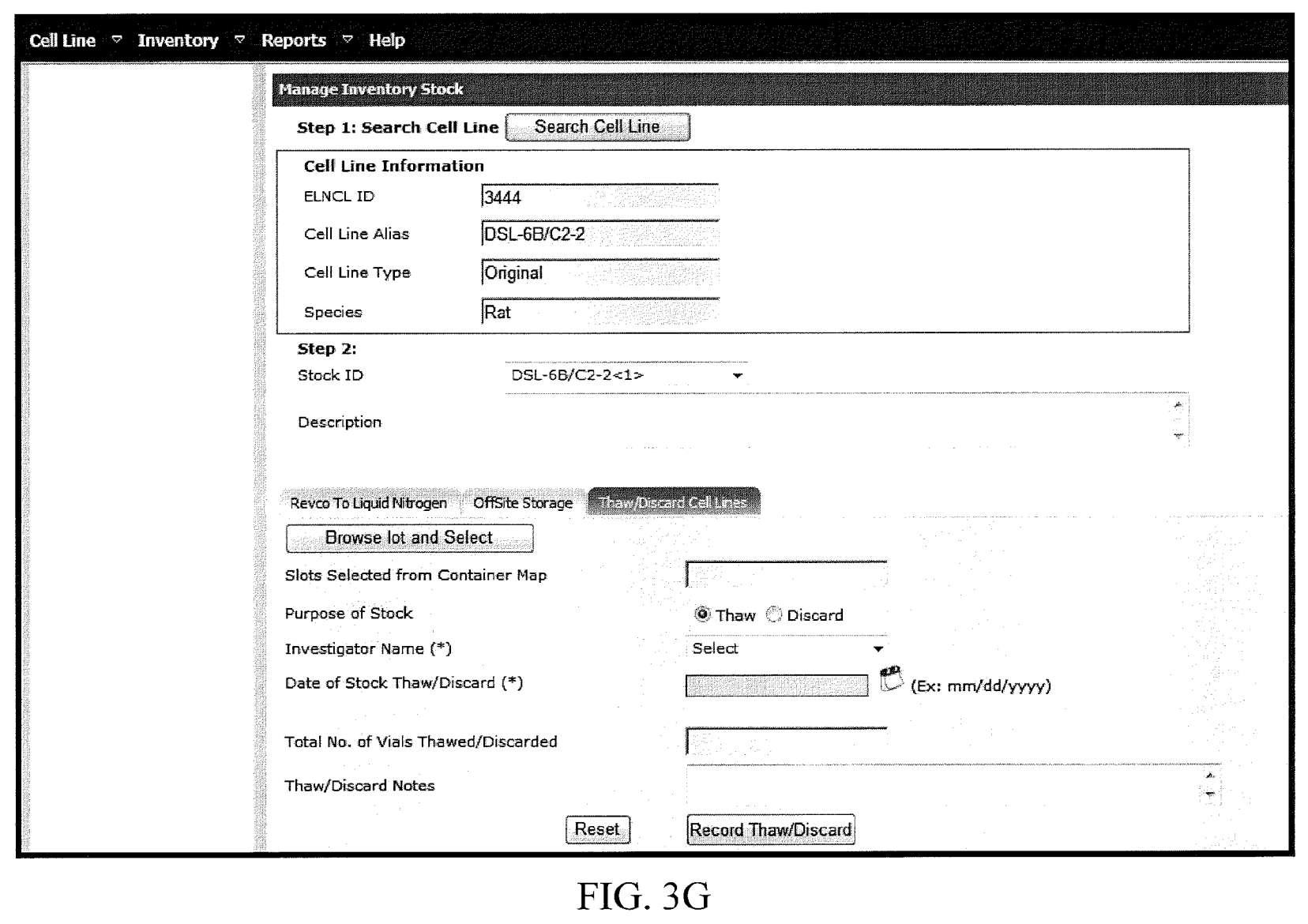
Figure 3H:
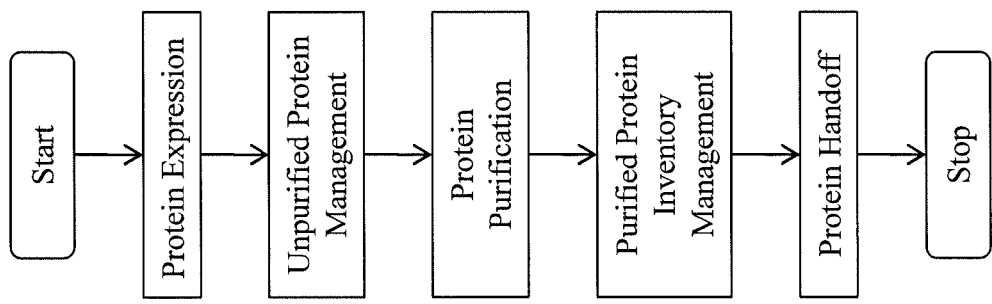
FIG. 3H illustrates an exemplary workflow of a biological process.

For searching biological processes, biological process inputs, outputs, and their derived forms user's need to provide a set of inputs for searching. A set of results is returned based on the provided set of inputs. The results obtained can be viewed/modified via user interface 302. In an embodiment of the present invention, the set of inputs includes details related to properties of biological process inputs, outputs and their processes, inputs for one or more of biological process inputs, outputs and their derived forms such as name, type, species, tissue type, description and inputs related to one or more biological processes. Examples of the inputs for associated biological processes include, but are not limited to, inputs for hybridoma development, transfection, adaptation, amplification, purification, characterization and cloning. FIG. 3B illustrates an exemplary screenshot for searching biological process, biological process inputs, outputs and their derived forms. As illustrated, the search can be conducted by providing a set of inputs. On providing the set of inputs a set of results is returned. As illustrated, the set of results includes details related to biological process inputs, outputs and their derived forms identified based on the set of inputs.

Presentation tier 304 interacts with middle tier 306 and database 314 for rendering information. Middle tier 306 is configured to process information related to the biological processes and biological process inputs, outputs and their derived forms. The processing of information includes modifying the information captured via presentation tier 304, wherein the information is modified to predefined formats. In an embodiment of the present invention, the processing of information is performed for registering biological processes, biological process inputs, outputs and their derived forms, developing genealogy maps, developing container maps, modifying details of biological processes and process inputs, outputs and their derivatives, tracking biological process inputs, outputs and their derived forms, registering inventory of biological process inputs, outputs and their derived forms, tracking inventory of biological process inputs, outputs and their derived forms, procurement requests for biological process inputs, outputs and their derived forms, depleting biological process inputs, outputs and their derived forms, creating workflows for biological processes, searching for a biological process, biological process inputs, outputs and their derived forms and collaborating information related to biological processes, biological process inputs, outputs and their derived forms.

Middle tier 306 includes service tier 328, business logic tier 330 and data access tier 332. Service tier 328 is configured to provide one or more services. In an embodiment of the present invention, the one or more services are provided as a web service via a web service module. The one or more services include, but are not limited to, a service to store data in EAV model, a service to retrieve data from EAV model, inventory service, and one or more services for managing workflows.

The registration service is provided in conjunction with business logic tier 330. The registration service enables recording and registering of biological process inputs, outputs and their derived forms such as, but not limited to, cell lines, plasmids, antibodies and proteins. In an embodiment of the present invention, registration of biological process, biological process inputs, outputs and their derived forms includes capturing registration information about the biological process inputs, outputs and their derived forms including a predefined set of details in a predefined format via user interface 302. The captured registration information is used for registering the biological process inputs, outputs and their derived forms. FIG. 3C illustrates an exemplary screenshot for recording and registering biological processes, biological process inputs, outputs and their derived forms. As illustrated, for registering a parent cell line the information captured includes cell line information and notebook information. The cell line information includes cell line name, species, tissue type, percent transfection efficiency and description of the cell line. The notebook information includes project name, project ID, investigator name, notebook name, notebook page number and notebook details. The notebook information further includes information related to the growth conditions such as carbon dioxide levels, number of units, temperature level and so forth. The notebook information also includes tracking information such as alert values, number of units being used, tracking number and so forth. The parent cell line is registered based on the cell line information provided.

Business logic tier 330 enables managing information of derived forms of biological processes, biological process inputs, outputs and their derived forms, wherein the details related to the linkages with one or more biological processes, biological process inputs, outputs and their derived forms are recorded. This enables interlinking of one or more biological process inputs, outputs and their derived forms. Further, in the biological processes the attributes and properties of the biological process outputs undergo changes. The changes are captured and stored via user interface 302. In biological processes, one or more batches of biological process outputs can be modified. Further, a set of batches of stock of biological process inputs, outputs and their derived forms are generated based on the biological processes. The information related to the batches of biological process inputs, output and their derived forms is stored in database 314. Further, the information can be accessed and modified via user interface 302.

The inventory service enables managing inventory of biological process inputs, outputs and their derived forms. In various embodiments of the present invention, the system includes an inventory module for managing and tracking the inventory of the biological process inputs, outputs and their derived forms. Managing inventory of biological process inputs, outputs and their derived forms includes registering inventory of biological process inputs, outputs and their derived forms and tracking changes in their inventory. Recording the inventory of biological process inputs, outputs or their derived forms includes selecting biological process, biological process inputs, outputs or their derived forms for which inventory information needs to be captured and subsequently capturing registration information of the selected biological process, biological process inputs, outputs or their derived forms. The inventory registration information includes a predefined set of details in a predefined format. In an embodiment of the present invention, the predefined set of details includes, but is not limited to, stock information, container information, depletion information and off-site storage information. For example, container information including number of units of biological process inputs, output or their derived forms, container type for storing the biological process output or their derived forms, freezer ID, sample number/cane number, pie number, box number and container notes is used for registering a biological process output or a derived form stock to a container. The captured inventory registration information is used for registering inventory of the biological process input, output or the derived form. For example, inventory information for cell lines derived from a cloning process or for a protein processed via a protein purification process is captured. The inventory information is also audited for checking spillage, degradation and incorrect data entry. The system further provides graphical representation of different freezers and containers for facilitating users to visually select slots in order to assign, reassign, move, deplete and add biological process inputs, outputs and their derived forms. In an embodiment of the present invention, the inventory module enables bulk upload of samples of biological process inputs, outputs and their derived forms into freezer locations. Further, the inventory module enables fulfillment of requests for one or more biological process inputs, outputs and their derived forms. The check in and check out to suitably manage a global and local freezer stock is also maintained. Also, the inventory module enables reassigning stocks within, between freezers or different type of freezers. The inventory details of one or more freezers includes information related to shelves, boxes, stacks, pies, slots and so forth.

The tracking of inventory of biological process inputs, outputs and their derived forms is performed by monitoring the inventory levels of the biological process inputs, outputs and their derived forms. In an exemplary embodiment of the present invention, the tracking is performed by tracking vials containing biological process input, output and derived forms of biological process outputs. The inventory information is updated based on the depletion, thawing or discarding of biological process inputs, outputs and their derived forms. Further, the inventory information can be accessed via user interface 302. In an embodiment of the present invention, each biological process input, output and derived form is assigned a sample number and a bar-code, which is used for tracking the biological inputs, output or derived forms. In another embodiment of the present invention, Radio-Frequency Identification (RFID) is used for tracking biological process inputs, outputs and their derived forms, wherein an RFID tag is attached to each biological process inputs, output and its derived forms. Tagging the biological process inputs, outputs and their derived forms enables identification and tracking via radio waves and automated update of database.

The inventory service also enables creation and viewing of container maps of biological process inputs, outputs or derived forms of biological process outputs. The container maps are created based on container information identified from inventory information of biological process inputs, outputs and their derived forms. In an exemplary embodiment of the present invention, the inventory details of biological process inputs, outputs and their derived forms stored in one or more freezers is managed, wherein details related to the biological process output and their derived forms stored in vials is maintained and updated based on usage. Details related to stocks of biological process output and their derived forms are tracked via sample numbers and barcodes. Further, the details are used to create container maps for the biological process inputs, outputs and their derived forms.

FIGS. 3D, 3E, 3F and 3G illustrate exemplary screenshots for managing inventory of biological process inputs, outputs and their derived forms. As illustrated, the biological process output inventory is registered by selecting the corresponding biological process output. Further, the inventory details of biological processes, biological process inputs, outputs and their derived forms can be accessed by searching for the corresponding biological processes, biological process inputs, outputs and their derived forms. Thereafter, the inventory information can be modified for the corresponding biological processes, biological process inputs, outputs and their derived forms. The inventory information, as illustrated in FIG. 3D includes cell line stock, information, cell line process output information, container information, container map information, depletion information and off site inventory information.

The inventory service also enables procurement of biological process output or derived forms based on requests in a predefined format including a predefined set of details. The inventory information is updated based on the fulfillment of the requests. In an exemplary embodiment of the present invention, system 300 includes a record-register-request module that enables vendors to record, register and request biological process inputs, outputs and their derived forms. The record-register-request module also supports byproducts or materials required in biological processes. Further, the vendors provide a list or catalogue of products including biological process inputs, outputs and their derived forms. The users such as scientists including biologists, chemists etc. can request for products from the list of products through the record-register-request module. Based on the fulfillment of the request, the details related to products procured and the associated inventory details can be updated in system 300. The details of the requested products can also be modified based on the information received from the vendors. Further, the details can be updated based on shipping back of the products.

The workflow service enables creation of workflows for biological processes. In an embodiment of the present invention, the workflows are created from predefined workflows. For example, workflows are created from workflows defined for registering biological processes, biological process inputs, outputs and their derived forms, modifying information of biological process inputs, outputs and their derived forms, tracking biological process inputs, outputs and their derived forms and so forth. The created workflows are stored in database 314 and can be accessed via user interface 302. Infrastructure module 308 is configured to process the created workflows. The processing of workflows includes providing a predefined level of security to the created workflows, creating metadata for the workflows and validating the created workflows. FIG. H illustrates an exemplary workflow of a biological process. The exemplary workflow represents a protein purification process.

Business logic tier 330 of middle tier 306 processes information related to biological process, biological process inputs, outputs and their derived forms which include cell lines, plasmids, antibodies and proteins and their derived forms. In an embodiment of the present invention, business logic tier 330 includes a registration module for registering biological processes, biological process inputs, outputs and their derived forms. The registration is performed by assigning a unique identified to each biological process, biological process output and derived form. Further, the biological processes, biological process inputs, outputs and their derived forms are registered via the registration service provided through service tier 326. The registration of biological process inputs, outputs and their derived forms are validated via a validation service provided through a validation module, in accordance with another embodiment of the present invention. In various embodiments of the present invention, the validation is performed to check the uniqueness and accuracy of the registration data.

The processing of information includes capturing information related to registration of biological process, biological process output and their derived forms, modifications in biological process, biological process output and their derived forms, genealogy of biological process inputs, outputs and their derived forms, inventory of biological process inputs, outputs and their derived forms and processes performed on the biological process inputs, outputs and their derived forms. The processing further includes modifying the captured information into a predefined format and subsequently storing the modified information in database 314.

The biological process outputs are modified through biological processes such as transfection, transduction, adaptation, amplification, hybridization and so forth. As a result of the biological processes derived forms of biological process outputs are obtained. New biological process outputs may also be created from the biological processes. The information related to the biological processes and the modifications in biological process outputs is captured and stored in database 314. For example, for an adaptation process performed on a cell line details such as derived cell line name, parent cell line name, parent species, parent tissue type, description of the adaption process and so forth are captured and stored.

Further, information related to the derived forms of biological process outputs and new biological process outputs are also captured and stored in database 314. The processing also includes registering of the biological process outputs, the derived forms of biological outputs and new biological process outputs. The genealogy of biological process inputs, outputs and their derived forms are also captured, wherein the genealogy of a biological process output and the derived forms represents the relationship between the biological process inputs, outputs and the derived forms. In an exemplary embodiment of the present invention, genealogy maps are created using a Resource Description Framework (RDF). In another exemplary embodiment of the present invention, genealogy maps are created using a Web Ontology Language (OWL). Business logic tier 330 also enables capturing performance details of biological process inputs, outputs and their derived forms, which is stored in database 314. The performance of biological process inputs, outputs and their derived forms in one or more assays is captured and stored. Further, the performance information can be depicted in predefined formats such as reports, graphs, charts and so forth. Thereafter, the corresponding information can be accessed via user interface 302.

It will be apparent that storing of information related to biological process inputs, outputs and their derived forms and the associated biological processes enables tracking modifications in biological process inputs, outputs and their derived forms. The information related to biological process inputs, outputs and their derived forms and the associated biological processes can be accessed via user interface 302. Further, storing the information in predefined formats enables collaboration of information, which can be subsequently accessed via user interface 302.

The information processed by service tier 328 and business logic tier 330 is used by data access tier 332. Data access tier 332 is configured to provide data services, a mapping process and a framework component. Data services include services for analyzing information, generating reports for the information, creating visual representations such as graphs, charts etc. based on the information and so forth. Data services enable storage of information of biological process, biological process inputs, outputs and their derived forms. The information stored includes information related to attributes and properties of biological process inputs, outputs and their derived forms. The information stored further includes instance values of biological process inputs, outputs and their derived forms. It will be apparent that data services enable structural storage of data that enables efficient collaboration of information.

The mapping process is used for developing genealogy maps for biological process inputs, outputs and their derived forms. In an embodiment of the present invention, the genealogy of biological process inputs, outputs and their derived forms captured via business logic tier 330 is used for developing genealogy maps. The developed genealogy maps are stored in database 314 and can be accessed via user interface 302.

The framework component is configured to enable access to the information related to biological processes, biological process inputs, outputs and their derived forms and the data service. In an exemplary embodiment of the present invention, the framework component is an ADO.net® component.

The framework component interacts with enterprise library 310 for enabling access of the related information and data services. Enterprise library 310 includes a set of predefined components developed for enabling one or more of, but not limited to, data exception handling, data blocking, data logging, data caching, data validation and data access. In an exemplary embodiment of the present invention, enterprise library 310 is a Microsoft® Enterprise Library.

Middle tier 306 also interacts with third party module 312 for managing information related to biological processes. Third party module 312 includes a third party interface 334, a third party reports module 336, a third party server 338 and a third party web player 340. Third party module 312 is configured to provide a set of features for managing information of biological processes, biological process inputs, outputs and their derived forms. The set of features include, but are not limited to, analyzing information related to biological process inputs, outputs and their derived forms, generating reports for the analyzed information and so forth.

Third party interface 334 provides an interactive interface for accessing the set of features provided by the third party module. In an exemplary embodiment of the present invention, third party interface 334 is a SciTegic® Pipeline Pilot Web Port Client.

Third party reports module 336 is configured to analyze biological information and generate reports based on the analysis. In an exemplary embodiment of the present invention, third party reports module 336 is a SciTegic® Pipeline Pilot data analytics and reporting module.

Third party server 338 is configured to enable managing information via third party interface 334 and third party reports module 336. Third party server 338 provides a set of services for configuration, integration, deployment and administration of information. In an exemplary embodiment of the present invention, third party server 338 is a Spotfire® Analytics Server.

Third party web player 340 is configured to provide an interactive interface for exchange of information between users and third party module 312. Third party web player 340 enables access of the set of services provided by third party server 338 via user interface 302. In an exemplary embodiment of the present invention, third party web player 340 is a Spotfire® Web Player.

System 300 includes server 316 for managing information related to the biological processes. In an embodiment of the present invention, server 316 is a Structured Query Language (SQL) server. In an exemplary embodiment of the present invention, server 316 is a Microsoft® Office SharePoint Server. In various embodiments of the present invention, server 316 is a server infrastructure configured to facilitate communication between one or more users and the system through the user interface module.

Database 314 is configured to store information related to the biological processes, biological process inputs, outputs and their derived forms. In an embodiment of the present invention, database 314 includes a set of tables for biological process, biological process inputs, outputs and their derived forms. For example, database 314 includes tables for cell lines, plasmids, antibodies and proteins. The tables include various columns for storing information related to the biological processes, biological process inputs, outputs and their derived forms. For example, for a cell line, the table includes columns for cell line name, type, species, details and so forth.

Database 314 is also configured to interact with data warehouse 318 which is configured to support analysis of stored information and generation of reports. In an embodiment of the present invention, data warehouse 318 includes one or more data marts such as data mart1 and data mart2, one or more data cubes such as data cube1 and data cube2 and a meta data store. The data marts are analytical data stores designed to support managing of information. The data cubes are components within data warehouse 318 with multi-dimensional array of values designed for representing information related to images. The meta data store stores design-time metadata. Data warehouse 318 interacts with third party module 312 for supporting analysis of stored information and generation of reports.

Figure 4A:
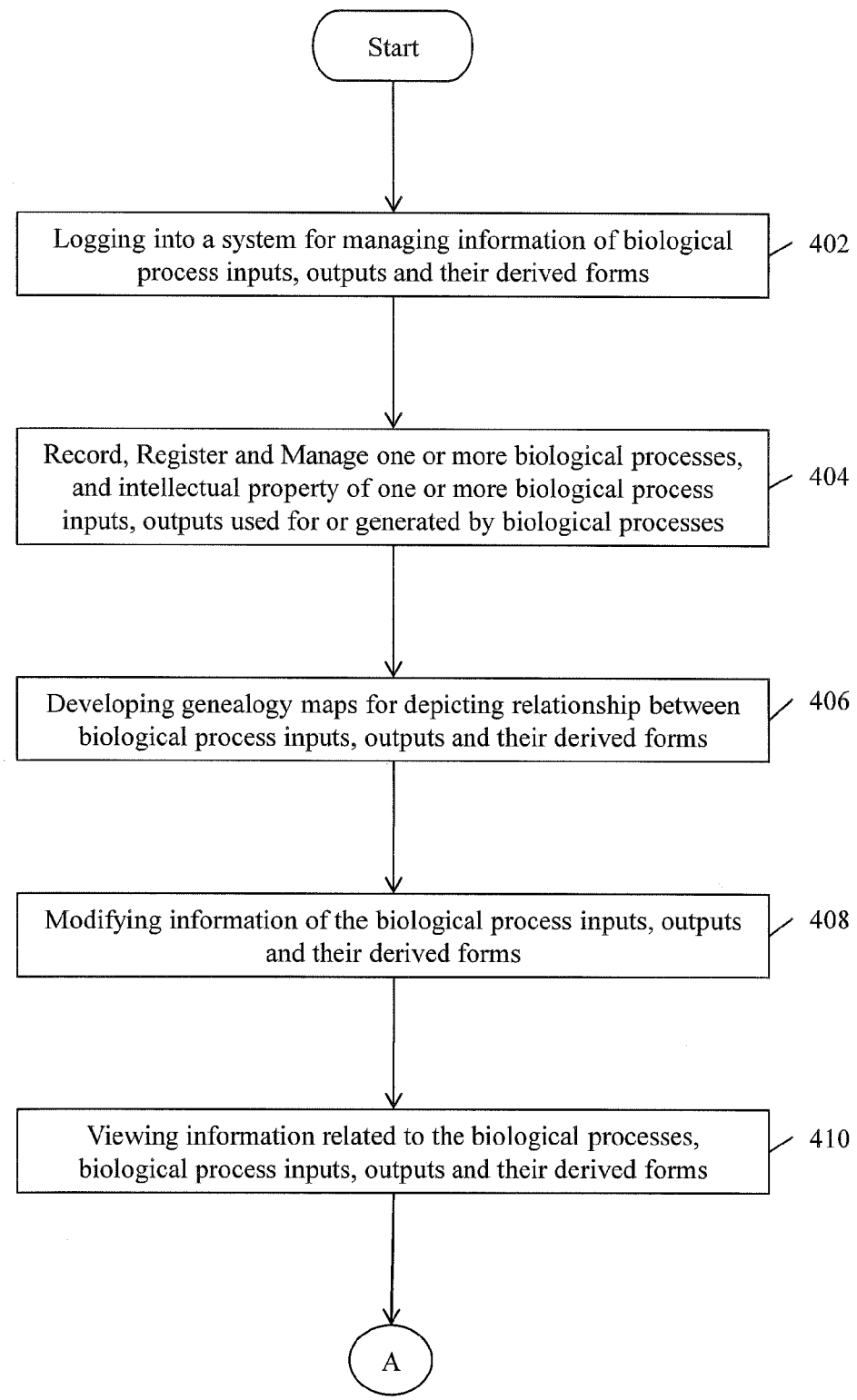
FIGS. 4A and 4B illustrate a flowchart of a method for managing, tracking and recording one or more biological process inputs, outputs and their derived forms, in accordance with an embodiment of the present invention.
Figure 4B:
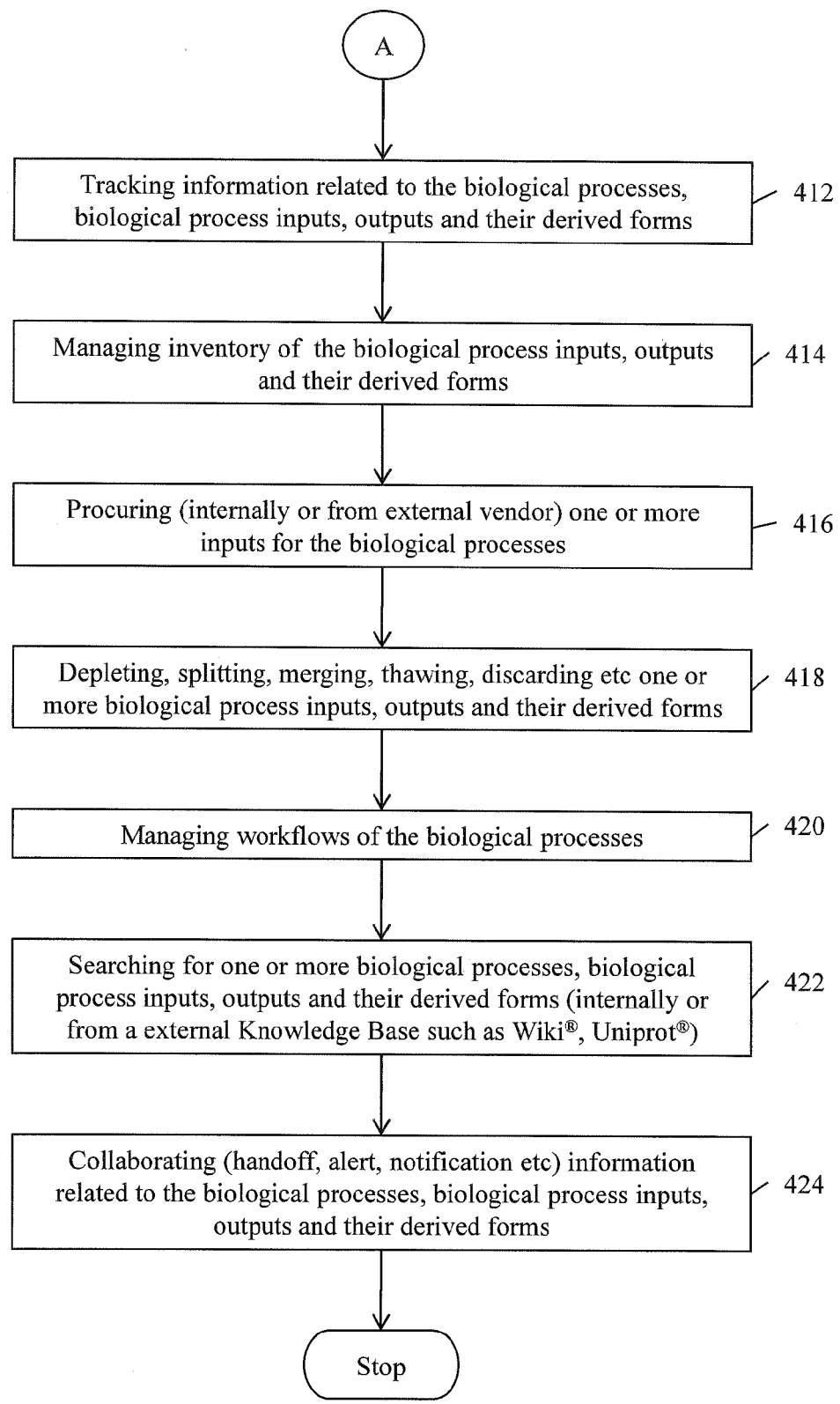

FIGS. 4A and 4B illustrate a method for managing and tracking of one or more biological process inputs, outputs and their derived forms, in accordance with an embodiment of the present invention.

At step 402, a user logs in for managing and tracking information of biological process inputs, outputs and their derived forms. In an embodiment of the present invention, the user logs in via a user interface. Examples of user interface include, but are not limited to, a Graphical User Interface (GUI) and a web based user interface. The user provides login and password details for logging in. The login and password details are validated and a customized user interface is rendered to the user.

In an embodiment of the present invention, the customized user interface includes a predefined set of components. Each component of the predefined set of components enables access of one or more features. In an embodiment of the present invention, the predefined set of components includes components for registration of biological process, the biological process inputs, outputs and derived forms of biological process outputs, developing genealogy maps for biological process inputs, outputs and their derived forms, modifying information of biological process, biological process inputs, outputs and their derived forms, viewing information of biological process, biological process inputs, outputs and their derived forms, tracking of biological process, biological process inputs, outputs and their derived forms, managing inventory of biological process inputs, outputs and their derived forms, enabling procurement and depletion of biological process inputs, outputs and their derived forms, searching for biological process, biological process inputs, outputs and their derived forms and viewing collaborated information of various biological processes and biological process inputs, outputs and their derived forms.

At step 404, one or more biological processes are recorded, registered and managed. In various embodiments of the present invention, the intellectual property of one or more biological process inputs, outputs used for or generated by biological processes is recorded and managed. The one or more biological processes, biological process inputs, outputs and their derived forms are registered. The user accesses one or more components of the predefined set of components for registering these biological processes, its outputs and their derivatives. Further, a predefined set of inputs are provided for registering each of them. The registration is performed based on the predefined set of inputs and the registered biological processes, biological process inputs, outputs and their derived forms are stored in a database.

At step 406, one or more genealogy maps are developed for biological process inputs, outputs and their derived forms. Genealogy maps are developed by accessing one or more components of the predefined set of components. The developed genealogy maps are stored in the database.

At step 408, information related to one or more output of biological process inputs, outputs is modified. The biological process outputs are modified by one or more biological processes, which leads to generation of derived forms of biological process outputs. New biological process outputs may also be generated via these biological processes. The derived forms of the biological process outputs and the new biological process outputs generated are registered and the information related to the corresponding biological processes is recorded.

At step 410, information related to biological processes, biological process inputs, outputs and their derived forms is viewed. The user accesses one or more components of the predefined set of components to view the related information. For example, the user can view information related to the biological process outputs, derivative forms of biological process outputs, biological processes and so forth.

At step 412, tracking of information related to biological processes is performed. Tracking includes identifying modifications in output of biological process and thereafter recording the corresponding modifications. Tracking provides information such as the biological processes performed on a biological process output, usage of output of biological process, performance of output of biological process and so forth.

At step 414, inventory of biological process inputs, outputs and their derived forms is managed. The managing of inventory includes registering inventory of biological process inputs, outputs and their derivative forms and thereafter tracking their usage. The inventory of biological process inputs, outputs and their derived forms are registered by inputting a predefined set of inputs for the inventory of biological process inputs, outputs and their derived forms, wherein the predefined set of inputs includes, but is not limited to, biological process inputs, outputs and their derived forms information and inventory details such as name, type, species, tissue type, quantity and so forth. Further, inventory information is updated based on usage of biological process inputs, outputs and their derived forms, wherein the inventory information is modified upon procurement and depletion of biological process inputs, outputs and their derived forms. In an embodiment of the present invention, tracking of biological process inputs, outputs and their derived forms is performed by assigning sample numbers, bar-codes and RFID tags to the corresponding biological process inputs, outputs and their derived forms.

In an embodiment of the present invention, container maps are created for biological process inputs, outputs and their derived forms. The container maps provide visual representation of the inventory levels of biological process inputs, outputs and their derived forms stored in one or more containers. The container maps are created based on a predefined set of inputs related to container information of biological process inputs, outputs and their derived forms captured during its registration.

At step 416, procurement of one or more biological process inputs, outputs and their derived forms is performed. In an embodiment of the present invention, the procurement is performed internally by collecting biological process inputs, outputs and their derived forms stored in the freezers. In another embodiment of the present invention, the procurement is performed through external vendors.

Procurement of biological process inputs, outputs and their derived forms includes requesting of biological process inputs, outputs and their derived forms in a predefined format and subsequent fulfillment. The request for procuring is placed via the user interface.

At step 418, one or more biological process inputs, outputs and their derived forms are depleted. The depletion is performed based on depletion, splitting, merging, thawing; discarding etc. of biological process inputs, outputs and their derived forms, the inventory information is modified via the user interface. Thereafter, information related to the inventory depletion such as thawing date and description is updated.

At step 420, workflows of biological processes are managed. The managing of workflows includes creation of workflows and subsequent updates in workflows based on modifications. In an embodiment of the present invention, the workflows are created based on a predefined set of workflows. The workflows are modified based on the biological processes performed. The user creates the workflows via the user interface. Further, the user accesses the created workflows via the user interface. The admin user will also have the option to customize or change the workflow as per his/her requirements. For example if a purification workflow doesn't have an approval step it can be added at runtime by an admin user.

At step 422, search is performed for identifying information related to the biological processes, biological process inputs, outputs and their derived forms. The search is performed by providing a set of inputs via the user interface. The set of inputs are used to identify the biological process and biological process inputs, outputs and their derived forms. A set of results including the identified biological process, biological process inputs, outputs and their derived forms is rendered via the user interface. In an exemplary embodiment of the present invention, the user can define search criteria for performing the search. Further, the searches performed by a user can be saved and retrieved. In various embodiments of the present invention, the search is performed on a knowledge base of biological process outputs. The knowledge base is one of, but not limited to, an internal knowledge base and an external knowledge base.

At step 424, collaborating of information related to biological processes, biological process inputs, outputs and their derived forms is performed. The collaborated information includes information related to the biological processes, the biological process inputs, outputs and their derived forms. Further, the collaborated information includes information related to handoff, alert, notification and so forth. The collaborated information related to biological processes, biological process inputs, outputs and their derived forms is viewed by users for scientific research. The information related to various output of biological process, biological process inputs, outputs and their derived forms is collaborated and stored in the database. The user accesses the collaborated information via the user interface, wherein the user can view the analysis performed on biological process inputs, outputs and their derived forms and the reports generated.

The method for managing, tracking and recording the biological process inputs, outputs and their derived forms can be performed by performing one or more steps described above. Further, the steps can be performed in any order and need not be limited to the order described above.

The system for managing information of biological entities or any of its components may be embodied in the form of a computer system. Typical examples of a computer system includes a general-purpose computer, a programmed microprocessor, a micro-controller, a peripheral integrated circuit element, and other devices or arrangements of devices that are capable of implementing the steps that constitute the method of the present invention.

The computer system comprises a computer, an input device, a display unit and the Internet. The computer further comprises a microprocessor. The microprocessor is connected to a communication bus. The computer also includes a memory. The memory may include Random Access Memory (RAM) and Read Only Memory (ROM). The computer system further comprises a storage device. The storage device can be a hard disk drive or a removable storage drive such as a floppy disk drive, optical disk drive, etc. The storage device can also be other similar means for loading computer programs or other instructions into the computer system. The computer system also includes a communication unit. The communication unit allows the computer to connect to other databases and the Internet through an I/O interface. The communication unit allows the transfer as well as reception of data from other databases. The communication unit may include a modem, an Ethernet card, or any similar device which enables the computer system to connect to databases and networks such as LAN, MAN, WAN and the Internet. The computer system facilitates inputs from a user through input device, accessible to the system through I/O interface.

The computer system executes a set of instructions that are stored in one or more storage elements, in order to process input data. The storage elements may also hold data or other information as desired. The storage element may be in the form of an information source or a physical memory element present in the processing machine.

The set of instructions may include various commands that instruct the processing machine to perform specific tasks such as the steps that constitute the method of the present invention. The set of instructions may be in the form of a software program. Further, the software may be in the form of a collection of separate programs, a program module with a larger program or a portion of a program module, as in the present invention. The software may also include modular programming in the form of object-oriented programming. The processing of input data by the processing machine may be in response to user commands, results of previous processing or a request made by another processing machine.

While the exemplary embodiments of the present invention are described and illustrated herein, it will be appreciated that they are merely illustrative. It will be understood by those skilled in the art that various changes in form and detail may be made therein without departing from or offending the spirit and scope of the invention.

What is claimed is:

1. A system for managing, tracking and recording one or more biological process inputs, outputs and their derived forms, the system comprising:
   a user interface module in communication with a computer system and configured to receive inputs pertaining to each of the one or more biological process inputs, outputs and their derived forms, wherein the inputs comprise at least one of:
information related to the biological process;
information related to the one or more biological process inputs, outputs and their derived forms on which the biological process is performed;
information related to modifications in the one or more biological process inputs, outputs and their derived forms in the biological process; and
information related to the outputs of the biological process;
a processing module in communication with a microprocessor and configured to process the received inputs, wherein processing comprises modifying the received inputs into a predefined format, and wherein the processing module comprises a workflow module in communication with the microprocessor and configured to generate one or more workflows for each biological process based on the inputs received for the biological process;
an infrastructure module in communication with the computer system and configured to:
validate the generated one or more workflows based on one or more validation protocols;
add a predefined level of security to the generated workflows based on predefined conditions; and
create metadata for the generated workflows; and
a data repository in communication with the computer system and configured to store the received inputs and the processed inputs;
wherein the user interface module is further configured to access the inputs stored in the data repository.

2. The system of claim 1, wherein the information related to the biological processes comprises:
information which aids in executing the business process; and
information used for the business process and reactions in the biological processes.

3. The system of claim 1 further comprising a web service module in communication with the computer system and configured to facilitate interaction between one or more users and the system through the user interface module over a network.

4. The system of claim 1, wherein the processing module further comprises a registration module in communication with the microprocessor and configured to register by assigning a unique identifier to each of the one or more biological processes, biological process inputs, outputs and their derived forms.

5. The system of claim 4 further comprising a validation module in communication with the microprocessor and configured to validate the registered biological processes, biological process inputs, outputs and their derived forms based on uniqueness and accuracy of registration data.

6. The system of claim 1, wherein the data repository interacts with:
a data service module in communication with the computer system and configured to provide one or more data services for processing the received inputs;
a mapping module in communication with the computer system and configured to generate one or more genealogy maps for each of the one or more business process inputs, outputs and their derived forms, wherein each genealogy map represents the association between the corresponding biological process inputs, outputs and their derived forms and the outputs of the biological process; and
a framework component in communication with the computer system and configured to enable access of the stored inputs and the one or more data services.

7. The system of claim 6 is further configured to provide graphical representation of different freezers and containers for facilitating users to visually select slots in order to assign, reassign, move, deplete and add biological process inputs, outputs and their derived forms.

8. The system of claim 1, wherein the user interface module further comprises:
a biological process module in communication with the computer system and configured to render information related to the biological process, biological process inputs, outputs and their derived forms;
a dashboard and reports module in communication with the computer system and configured to render dashboards and reports generated for the one or more biological processes, biological process inputs, outputs and their derived forms; and
a service module in communication with the computer system and configured to render one or more services for managing, tracking and recording the biological process inputs, outputs and their derived forms, the one or more services comprising:
a collaboration service for collaborating information related to the one or more biological process, biological process inputs, outputs and their derived forms;
a document management service for managing the documents created for the one or more biological processes, biological process inputs, outputs and their derived forms; and
a search service for searching at least one of the one or more biological processes, biological process inputs, outputs and their derived forms.

9. The system of claim 8 further comprising a knowledge base of biological process inputs, outputs and derived forms configured to collaborate information related to the one or more biological processes, biological process inputs, outputs and their derived forms.

10. The system of claim 8, wherein the dashboards and reports generated for the biological processes, biological process inputs, outputs and their derived forms are represented in at least one of a tabular form and a graphical form.

11. The system of claim 8, wherein the search is performed based on inputs for one or more graphics stored in the data repository.

12. The system of claim 1 further comprising an inventory module in communication with the microprocessor and configured to manage inventory of the one or more biological process inputs, outputs and their derived forms, wherein managing the inventory comprises:
registering the inventory of the one or more biological process inputs, outputs and their derived forms;
updating the inventory details of the one or more biological process inputs, outputs and their derived forms based on:
modifications in the inventory of the one or more biological process inputs, outputs and their derived forms in the biological process; and
outputs of the biological processes; and
auditing the inventory details.

13. The system of claim 12, wherein the inventory module is further configured to:
bulk upload of samples of biological process inputs, outputs and their derived forms into freezer locations;
fulfill requests for one or more biological process inputs, outputs and their derived forms;

check in and check out to suitably manage a global and local freezer stock; and reassign stocks within, between or different type of freezers.

14. The system of claim 12, wherein the inventory module is further configured to:
generate one or more container maps for the one or more biological process inputs, outputs and their derived forms, wherein each container map represents storage information of the corresponding biological process inputs, outputs and their derived forms; and
manage the inventory details of one or more biological process inputs, outputs and their derived forms stored in one or more freezers.

15. The system of claim 14, wherein the inventory details of biological process inputs, outputs and their derived forms stored in one or more freezers comprise shelves, boxes, stacks, pies and slots information.

16. The system of claim 12, wherein the inventory module is further configured to update the inventory details based on:
procurement of one or more biological process inputs, outputs and their derived forms based on procurement inputs received through the user interface module; and
depletion of the one or more biological process inputs, outputs and their derived forms.

17. The system of claim 16, wherein the depletion of the one or more biological process inputs, outputs and their derived forms further comprises thawing and discarding of the biological process inputs, outputs and their derived forms.

18. The system of claim 1, wherein the data repository comprises:
an Entity-Attribute-Value model in communication with the computer system and configured to store information related to the biological processes, biological process inputs, outputs and their derived forms;
a relational data model in communication with the computer system and configured to store inventory details of the biological process inputs, outputs and their derived forms; and
a semantic model in communication with the computer system and configured to store relationships between the biological processes, biological process inputs, outputs and their derived forms.

19. The system of claim 1 further comprising a server infrastructure in communication with the computer system and configured to facilitate communication between one or more users and the system through the user interface module.

20. The system of claim 19, wherein the server infrastructure facilitates communication between the processing module and a third party module, the third party module comprising:
a third party interface in communication with the computer system and configured to render a set of features for managing and tracking the one or more biological process, biological process inputs, outputs and their derived forms;
a third party reports module in communication with the computer system and configured to analyze the information related to the biological processes, biological process inputs, outputs and their derived forms and generate reports based on the analysis;
a third party server in communication with the computer system and configured to facilitate the access of the set of features via the third party interface and the third party reports module; and
a third party web player in communication with the computer system and configured to provide an interactive interface for exchange of information between one or more users and third party module.

21. A computer-implemented method for managing, tracking and recording one or more biological process inputs, outputs and their derived forms, the method comprising:
gathering, using program instructions executed by a computer system, inputs pertaining to each of the one or more biological process inputs, outputs and their derived forms, wherein the inputs comprise at least one of:
information related to the biological process;
information related to the one or more biological process inputs, outputs and their derived forms;
information related to modifications in the one or more biological process inputs, outputs and their derived forms in the biological process; and
information related to outputs of the biological process;
processing, using program instructions executed by the computer system, the gathered inputs, wherein the processing comprises:
modifying the gathered inputs into a predefined format;
generating one or more workflows for each biological process based on the inputs received for the biological process;
validating the generated workflows based on one or more validation protocols;
adding a predefined level of security to the generated workflows based on predefined conditions; and
creating metadata for the generated workflows;
storing, using program instructions executed by the computer system, the gathered inputs and the processed inputs; and
viewing, using program instructions executed by the computer system, the stored inputs.

22. The method of claim 21 further comprises registering by assigning a unique identifier to each of the one or more biological processes, biological process inputs, outputs and their derived forms.

23. The method of claim 21, wherein processing the gathered inputs further comprises developing, using program instructions executed by a computer system, one or more genealogy maps for each of the one or more biological process inputs, outputs and their derived forms, wherein each genealogy map represents the association between the corresponding biological process inputs, outputs and their derived forms and the outputs of the biological process.

24. The method of claim 21 wherein processing the gathered inputs further comprises updating, using program instructions executed by a computer system, the information related to the one or more biological process inputs, outputs and their derived forms based on inputs related to one or more modifications in the one or more biological processes, biological process inputs, outputs and their derived forms.

25. The method of claim 24 further comprises tracking, using program instructions executed by a computer system, the one or more biological process inputs, outputs and their derived forms, wherein the tracking of the biological process inputs, outputs and their derived forms is performed by viewing the information related to the biological process, biological process inputs, outputs and their derived forms.

26. The method of claim 21 further comprises managing, using program instructions executed by a computer system, inventory of the one or more biological process inputs, outputs and their derived forms, wherein managing the inventory comprises:
registering, using program instructions executed by a computer system, the inventory of the one or more biological process inputs, outputs and their derived forms; and updating, using program instructions executed by a computer system, the inventory details of the one or more biological process inputs, outputs and their derived forms based on:
- modifications in the one or more biological process inputs, outputs and their derived forms in the biological process; and
- outputs of the biological processes.

27. The method of claim 26, wherein managing the inventory further comprises:
- generating, using program instructions executed by a computer system, one or more container maps for the one or more biological process inputs, outputs and their derived forms, wherein each container map represents storage information of the corresponding biological process inputs, outputs and their derived forms; and
- managing, using program instructions executed by a computer system, the inventory details of one or more biological process inputs, outputs and their derived forms stored in one or more freezers.

28. The method of claim 26 further comprises updating the inventory based on:
- procurement of one or more biological process inputs, outputs and their derived forms based on procurement inputs; and
- depletion of the one or more biological process inputs, outputs and their derived forms.

29. The method of claim 21 further comprises searching for at least one of the one or more biological processes, biological process inputs, outputs and their derived forms using program instructions executed by a computer system.

30. The method of claim 29, wherein the search is performed based on user-defined queries.

31. The method of claim 21 further comprises collaborating information related to the one or more biological process, biological process inputs, outputs and their derived forms using program instructions executed by a computer system, wherein collaborating the information comprises associating the information related to the one or more biological processes, biological process inputs, outputs and their derived forms.

32. A system for managing, tracking and recording one or more biological process inputs, outputs and their derived forms, the system comprising:
- a user interface module in communication with a computer system and configured to receive inputs pertaining to each of the one or more biological process inputs, outputs and their derived forms, wherein the inputs comprise at least one of:
  - information related to the biological process;
  - information related to the one or more biological process inputs, outputs and their derived forms on which the biological process is performed;
  - information related to modifications in the one or more biological process inputs, outputs and their derived forms in the biological process; and
  - information related to the outputs of the biological process;
- a processing module in communication with a microprocessor and configured to process the received inputs, wherein processing comprises modifying the received inputs into a predefined format, and wherein the processing module comprises a registration module in communication with the microprocessor and configured to register by assigning a unique identifier to each of the one or more biological processes, biological process inputs, outputs and their derived forms;
- a validation module in communication with the microprocessor and configured to validate the registered biological processes, biological process inputs, outputs and their derived forms based on uniqueness and accuracy of registration data; and
- a data repository in communication with the computer system and configured to store the received inputs and the processed inputs;
- wherein the user interface module is further configured to access the inputs stored in the data repository.

33. A computer-implemented method for managing, tracking and recording one or more biological process inputs, outputs and their derived forms, the method comprising:
- gathering, using program instructions executed by a computer system, inputs pertaining to each of the one or more biological process inputs, outputs and their derived forms, wherein the inputs comprise at least one of:
  - information related to the biological process;
  - information related to the one or more biological process inputs, outputs and their derived forms;
  - information related to modifications in the one or more biological process inputs, outputs and their derived forms in the biological process; and
  - information related to outputs of the biological process;
- processing, using program instructions executed by the computer system, the gathered inputs, wherein the processing comprises:
  - modifying the gathered inputs into a predefined format;
  - registering, by assigning a unique identifier to each of the one or more biological processes, biological process inputs, outputs and their derived forms;
  - validating the registered biological processes, biological process inputs, outputs and their derived forms based on uniqueness and accuracy of registration data;
- storing, using program instructions executed by the computer system, the gathered inputs and the processed inputs; and
- viewing, using program instructions executed by the computer system, the stored inputs.

* * * * *